(12) United States Patent
Wilke et al.

(10) Patent No.: US 10,835,278 B2
(45) Date of Patent: Nov. 17, 2020

(54) MEDICAL DEVICE SYSTEMS AND ACCESSORIES

(71) Applicant: BOSTON SCIENTIFIC SCIMED, INC., Maple Grove, MN (US)

(72) Inventors: Benjamin Michael Wilke, Circle Pines, MN (US); Debra M. Kozak, Forest Lake, MN (US); Michael P. Schrom, Forest Lake, MN (US); Daniel T. Quillin, Eden Prairie, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 338 days.

(21) Appl. No.: 15/900,105

(22) Filed: Feb. 20, 2018

(65) Prior Publication Data
US 2018/0235648 A1 Aug. 23, 2018

Related U.S. Application Data (60) Provisional application No. 62/461,553, filed on Feb. 21, 2017.

(51) Int. Cl.
*A61B 17/3203* (2006.01)
*A61B 17/22* (2006.01)
*A61M 25/00* (2006.01)

(52) U.S. Cl.
CPC ........ *A61B 17/32037* (2013.01); *A61B 17/22* (2013.01); *A61M 25/007* (2013.01);
(Continued)

(58) Field of Classification Search
CPC .............. A61B 17/22; A61B 17/32037; A61B 2017/22038; A61B 2017/22039;
(Continued)

(56) References Cited

U.S. PATENT DOCUMENTS

| 7,226,433 B2 | 6/2007 | Bonnette et al. |
| 8,998,843 B2 | 4/2015 | Bonnette et al. |

(Continued)

FOREIGN PATENT DOCUMENTS

| EP | 0788774 A1 | 8/1997 |
| EP | 1092396 A2 | 4/2001 |

(Continued)

OTHER PUBLICATIONS

International Search Report and Written Opinion for Application No. PCT/US2018/018762, 14 pages, dated Apr. 20, 2018.

*Primary Examiner* — Robert A Lynch
(74) *Attorney, Agent, or Firm* — Seager, Tufte & Wickhem LLP (57) ABSTRACT

Thrombectomy catheter systems, accessory devices, and methods for making and using such devices are disclosed. An example thrombectomy system may include a catheter shaft having a proximal portion, a distal portion, and a lumen extending at least partially through the catheter shaft. A high pressure tube may be disposed within the lumen. The high pressure tube may be designed for communication with a fluid source. A fluid jet emanator may be coupled to the high pressure tube. The fluid jet emanator may have at least one jet orifice. The catheter shaft may include a first orifice disposed proximally of a distal end of the catheter shaft and a second orifice disposed proximally of the first orifice. An accessory device may be disposed within the lumen. The accessory device may include a helical distal region.

20 Claims, 10 Drawing Sheets (52) U.S. Cl.
CPC ............ *A61M 25/0029* (2013.01); *A61B 2017/22038* (2013.01); *A61B 2017/22047* (2013.01); *A61B 2017/22079* (2013.01); *A61B 2017/22084* (2013.01); *A61B 2017/22094* (2013.01)

(58) Field of Classification Search
CPC .......... A61B 2017/22042; A61B 2017/22079; A61M 25/0029; A61M 25/005; A61M 25/007
See application file for complete search history.

(56) References Cited

U.S. PATENT DOCUMENTS

| | | |
|---|---|---|
| 9,078,691 B2 | 7/2015 | Morris et al. |
| 2005/0240146 A1 | 10/2005 | Nash et al. |
| 2006/0129091 A1* | 6/2006 | Bonnette ............... A61B 17/22 604/93.01 |
| 2007/0282303 A1 | 12/2007 | Nash et al. |
| 2008/0004643 A1* | 1/2008 | To ................... A61B 17/32075 606/159 |
| 2008/0058839 A1* | 3/2008 | Nobles .............. A61B 17/0057 606/148 |
| 2008/0097499 A1 | 4/2008 | Nash et al. |
| 2010/0145259 A1 | 6/2010 | Nash et al. |
| 2014/0163550 A1* | 6/2014 | Besser ............. A61M 25/0041 606/41 |
| 2014/0343595 A1 | 11/2014 | Monstadt et al. |
| 2015/0094748 A1 | 4/2015 | Nash et al. |
| 2016/0270814 A1* | 9/2016 | Palme .............. A61B 17/32075 |
| 2018/0000510 A1 | 1/2018 | Nash et al. |

FOREIGN PATENT DOCUMENTS

| | | |
|---|---|---|
| EP | 2712559 A2 | 4/2014 |
| WO | 9613295 | 5/1996 |
| WO | 2017152086 A1 | 9/2017 |

\* cited by examiner

MEDICAL DEVICE SYSTEMS AND ACCESSORIES

CROSS REFERENCE TO RELATED APPLICATIONS

This application claims the benefit of U.S. Provisional Patent Application Ser. No. 62/461,553 filed on Feb. 21, 2017, the disclosure of which is incorporated herein by reference.

TECHNICAL FIELD

The present disclosure pertains to medical devices, and methods for manufacturing medical devices. More particularly, the present disclosure pertains to medical device systems and accessory medical devices for use with the medical device systems.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a thrombectomy catheter system. The thrombectomy catheter system comprises a catheter shaft having a proximal portion, a distal portion, and a lumen extending at least partially through the catheter shaft; a high pressure tube disposed within the lumen, the high pressure tube being designed for communication with a fluid source; a fluid jet emanator coupled to the high pressure tube, the fluid jet emanator having at least one jet orifice; wherein the catheter shaft includes a first orifice disposed proximally of a distal end of the catheter shaft and a second orifice disposed proximally of the first orifice; and an accessory device disposed within the lumen, the accessory device including a helical distal region.

Alternatively or additionally to any of the embodiments above, the accessory device comprises a guidewire having a proximal region.

Alternatively or additionally to any of the embodiments above, the proximal region has a first diameter, wherein the helical distal region has a second diameter, and wherein the first diameter is different than the second diameter.

Alternatively or additionally to any of the embodiments above, the second diameter is larger than the first diameter.

Alternatively or additionally to any of the embodiments above, the proximal region has a first stiffness, wherein the helical distal region has a second stiffness, and wherein the first stiffness is different than the second stiffness.

Alternatively or additionally to any of the embodiments above, the second stiffness is greater than the first stiffness.

Alternatively or additionally to any of the embodiments above, the proximal region is attached to the helical distal region at a joint.

Alternatively or additionally to any of the embodiments above, the proximal region has a longitudinal axis and wherein the helical distal region extends from the proximal region at a non-zero angle relative to the longitudinal axis.

A thrombectomy catheter system is disclosed. The thrombectomy catheter system comprises a catheter shaft having a proximal portion, a distal portion, and a lumen extending at least partially through the catheter shaft; wherein the catheter shaft includes an inflow orifice disposed proximally of a distal end of the catheter shaft and an outflow orifice disposed proximally of the inflow orifice; and a guidewire disposed within the lumen, the guidewire including a proximal region and a helical distal region.

Alternatively or additionally to any of the embodiments above, the proximal region has a first diameter, wherein the helical distal region has a second diameter, and wherein the first diameter is different than the second diameter.

Alternatively or additionally to any of the embodiments above, the second diameter is larger than the first diameter.

Alternatively or additionally to any of the embodiments above, the proximal region has a first stiffness, wherein the helical distal region has a second stiffness, and wherein the first stiffness is different than the second stiffness.

Alternatively or additionally to any of the embodiments above, the second stiffness is greater than the first stiffness.

Alternatively or additionally to any of the embodiments above, the proximal region is attached to the helical distal region at a joint.

Alternatively or additionally to any of the embodiments above, the proximal region has a longitudinal axis and wherein the helical distal region extends from the proximal region at a non-zero angle relative to the longitudinal axis.

A method for orienting a catheter is disclosed. The method comprises disposing a thrombectomy catheter within a body lumen, the thrombectomy catheter comprising: a catheter shaft having a proximal portion, a distal portion, and a lumen extending at least partially through the catheter shaft, a high pressure tube disposed within the lumen, the high pressure tube being designed for communication with a fluid source, a fluid jet emanator coupled to the high pressure tube, the fluid jet emanator having at least one jet orifice, and wherein the catheter shaft includes a first orifice disposed proximally of a distal end of the catheter shaft and a second orifice disposed proximally of the first orifice; wherein disposing a thrombectomy catheter within a body lumen includes disposing the distal portion at a first position relative to a wall of the body lumen; disposing an accessory device within the lumen, the accessory device including a proximal region and a helical distal region; wherein disposing an accessory device within the lumen includes arranging the helical distal region so that at least a portion of the helical distal region is disposed adjacent to the wall of the body lumen; wherein disposing an accessory device within the lumen includes shifting the catheter shaft to a second position that is closer to the wall of the body lumen than the first position.

Alternatively or additionally to any of the embodiments above, shifting the catheter shaft to a second position includes moving the first orifice to a position adjacent to the wall of the body lumen.

Alternatively or additionally to any of the embodiments above, shifting the catheter shaft to a second position includes arranging at least a portion of the catheter shaft into a helical configuration.

Alternatively or additionally to any of the embodiments above, the proximal region of the accessory device has a first diameter, wherein the helical distal region has a second diameter, and wherein the second diameter is greater than the first diameter.

Alternatively or additionally to any of the embodiments above, the proximal region of the accessory device has a first stiffness, wherein the helical distal region has a second stiffness, and wherein the second stiffness is greater than the first stiffness.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Figure 1:
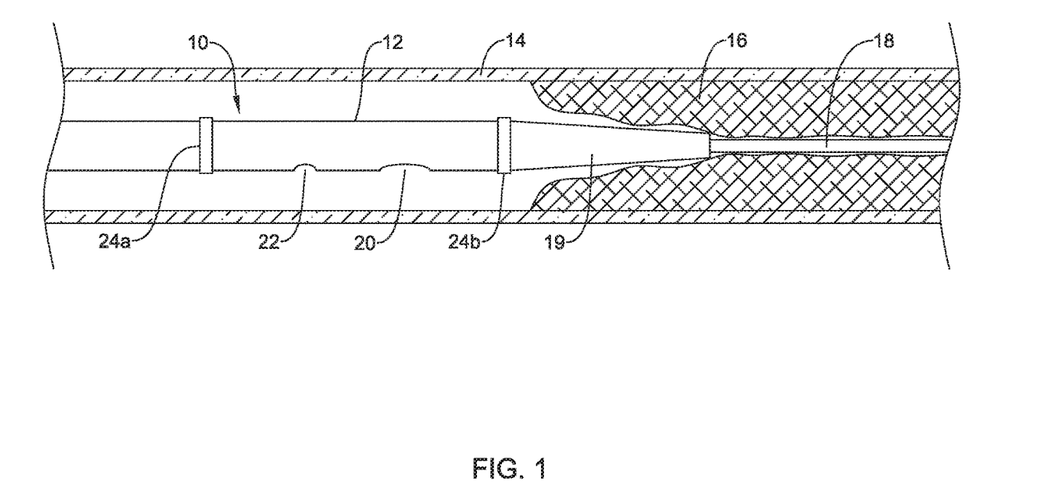
FIG. 1 is a partial cross-sectional side view of an example catheter system.

FIG. 1 illustrates an example medical device 10. In this example, the medical device 10 takes the form of a thrombectomy catheter. However, this is not intended to be limiting as other medical devices are contemplated. The thrombectomy catheter 10 may include a catheter shaft 12 that is designed to be used in a body lumen such as a blood vessel 14. The thrombectomy catheter 10 can be used, for example, to treat a lesion 16 (e.g., remove thrombus) in the blood vessel 14. To do so, the catheter shaft 12 may be advanced over a guidewire or accessory medical device 18 to a position adjacent to the lesion 16. For example, a distal tip region 19 of the catheter shaft 12 may be positioned adjacent to the lesion 16. While navigating the catheter shaft 12, one or more marker bands 24a/24b may be fluoroscopically monitored. When in the desired position, the thrombectomy catheter 10 can be used to disrupt or otherwise remove the lesion 16. This may include using a first or inflow orifice 20 and a second or outflow orifice 22 in the catheter shaft 12 as described in more detail below.

Figure 2:
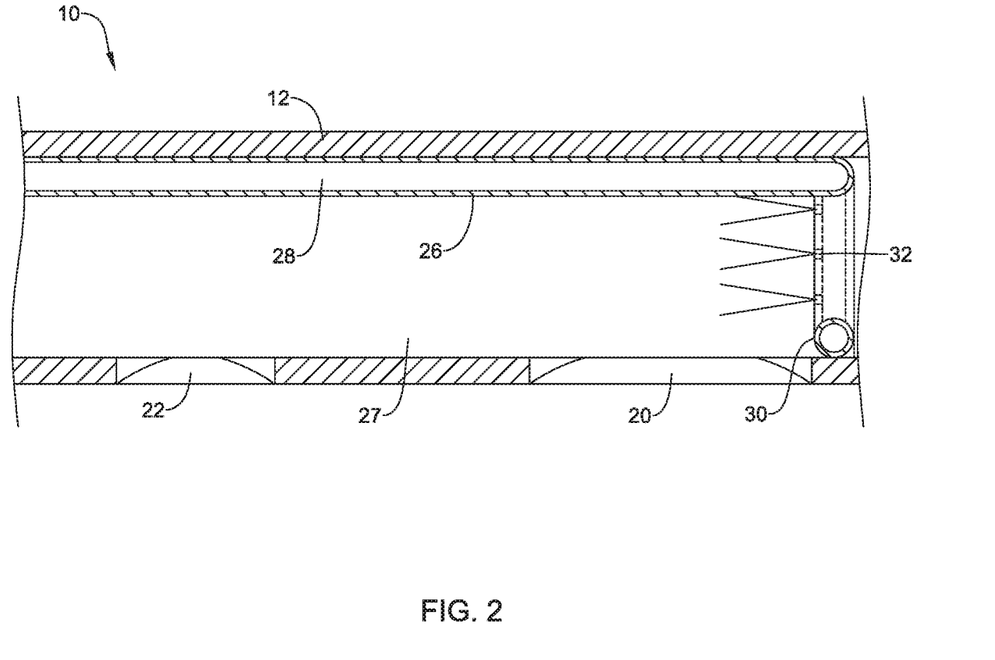
FIG. 2 is a cross-sectional side view of a portion of an example catheter.

FIG. 2 is a cross-sectional view of showing some of the components contemplated for the thrombectomy catheter 10. For example, the catheter shaft 12 may include an internal tubular member or high pressure tube 26 disposed within a lumen 27 of the catheter shaft 12. The high pressure tube 26 may include a lumen 28 that may be in fluid communication with a fluid source. A jet emanator 30 may be coupled to the high pressure tube 26. The jet emanator 30 may include one or more fluid jets 32. In general, the fluid jets 32 may be designed to inject fluid in a proximal direction within the catheter shaft 12. When doing so, areas of low pressure and fluid flow may cause material outside the catheter shaft 12 to flow into the lumen 27 of the catheter shaft 12 through the first orifice 20. The material can flow out of the second orifice 22, where the material may cycle back into the first orifice, sometime a plurality of times. Ultimately the material may be aspirated from the catheter shaft 12. These features are just examples of just one illustrative thrombectomy catheter. Other thrombectomy catheters are contemplated including those described in commonly assigned U.S. Pat. Nos. 8,998,843 and 9,078,691, which are herein incorporated by reference.

For a number of reasons, some areas within the blood vessel 14 may be difficult to access for the removal of thrombus. For example, in some instances thrombus may be positioned in close contact with the wall of the blood vessel 14. Because of the shape of traditional catheters and guidewires when fed into a blood vessel, it may be difficult to position a thrombectomy catheter in a desired position for efficiently removing such thrombus, such as thrombus close to the wall of the blood vessel 14. The devices and systems disclosed herein are designed to be positioned in a manner that allows for efficient removal of thrombus.

As indicated above, the thrombectomy catheter 10 may be used with an accessory device 18 (e.g., as a thrombectomy catheter system). The accessory device 18 may be a guidewire and, thus, may be used to navigate the catheter shaft 12 to the desired location within the blood vessel 14 and also may be used to position the catheter shaft 12 as described herein. Alternatively, the accessory device 18 may be a structure that is distinct from a guidewire. For example, a guidewire may be used to navigate the catheter shaft 12 to a desired location within the blood vessel 14. Thereafter, the guidewire can be removed and the accessory device 18 can be advanced through the catheter shaft 12. In both examples, the accessory device 18 may include one or more structural features that allow the catheter shaft 12 to be shifted or otherwise bent into a desired configuration for the removal of thrombus. For example, the accessory device 18 may be used to bend or curve the catheter shaft 12 so that the distal tip region 19 is positioned closer to the wall of the blood vessel 14. This may allow the catheter shaft 12 to efficiently remove the thrombus, for example thrombus that may be positioned at or near the wall of the blood vessel 14. In some of these and in other instances, the first orifice 20, the second orifice, or both may also be moved to a position that is closer to the wall of the blood vessel 14.

Figure 3:
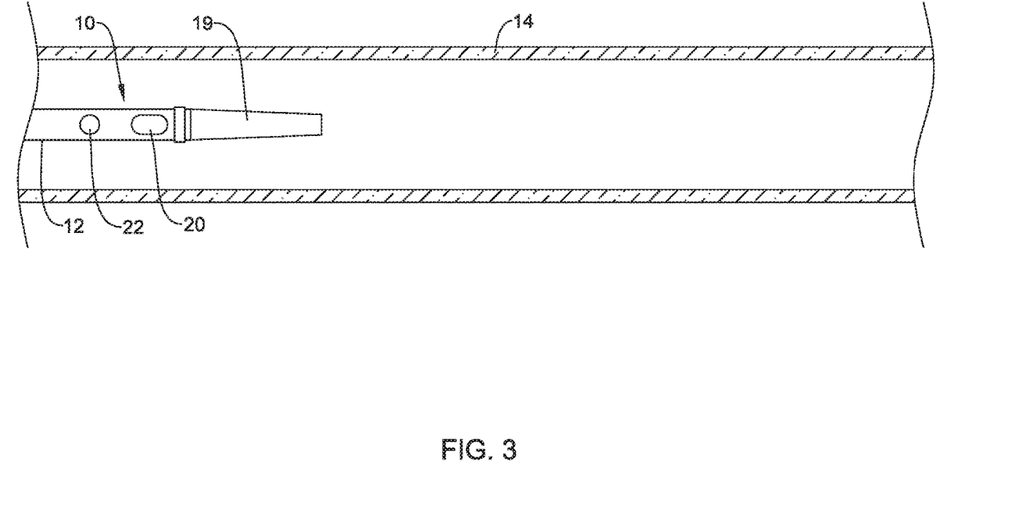
FIGS. 3-6 illustrate the use of an example catheter system.
Figure 4:
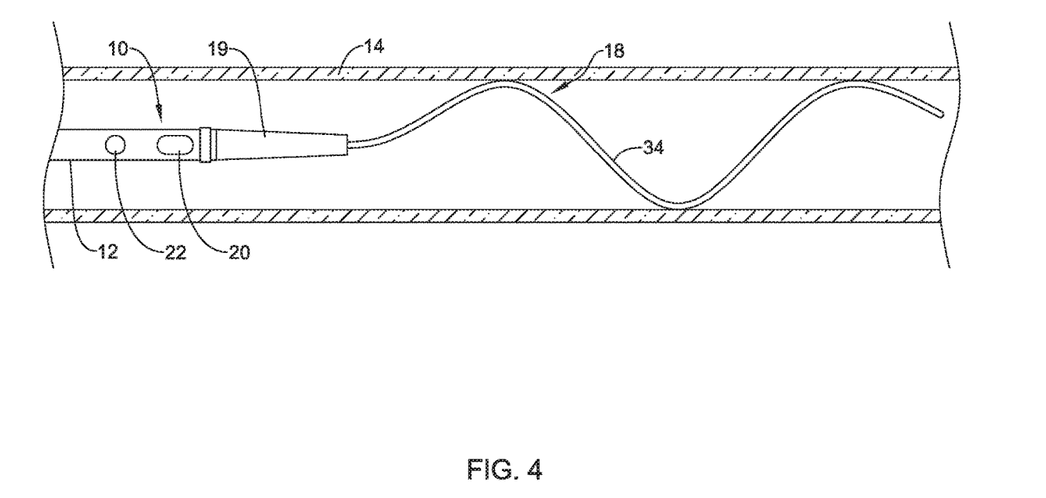

FIGS. 3-6 illustrate the use of the system 10. As shown in FIG. 3, the catheter shaft 12 may be advanced within the blood vessel 14. This may include advancing the catheter shaft 12 over a guidewire (not shown) and then removing the guidewire. In some instances, the catheter shaft 12 may be advanced over the accessory device 18 or the accessory device 18 may be disposed within the catheter 12 as depicted in FIG. 4. FIG. 4 also illustrates that the accessory device 18 may include a helical distal region 34. The helical distal region 34 may be arranged so that at least a portion thereof may be adjacent to or otherwise in contact with the wall of the blood vessel 14.

Figure 5:
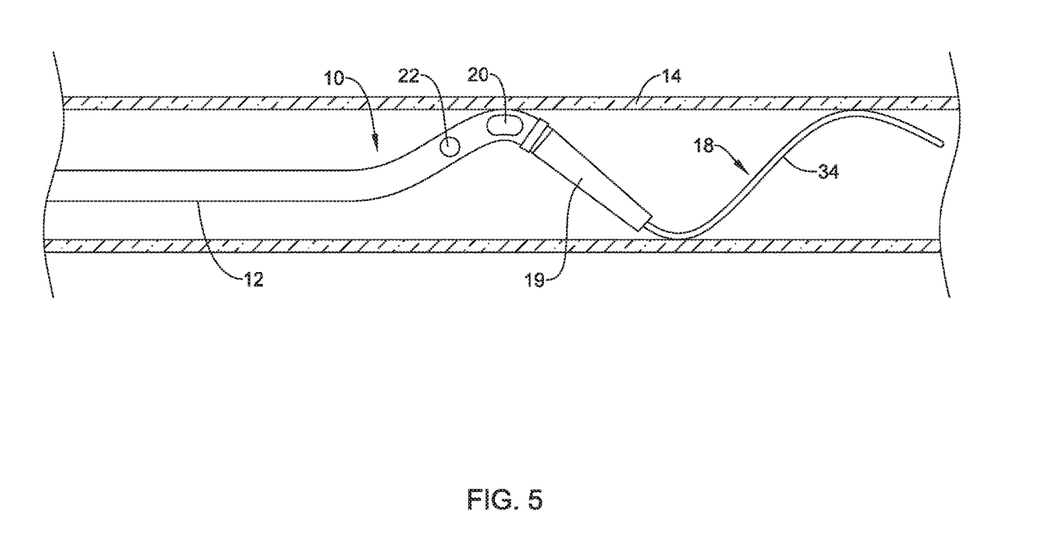
Figure 6:
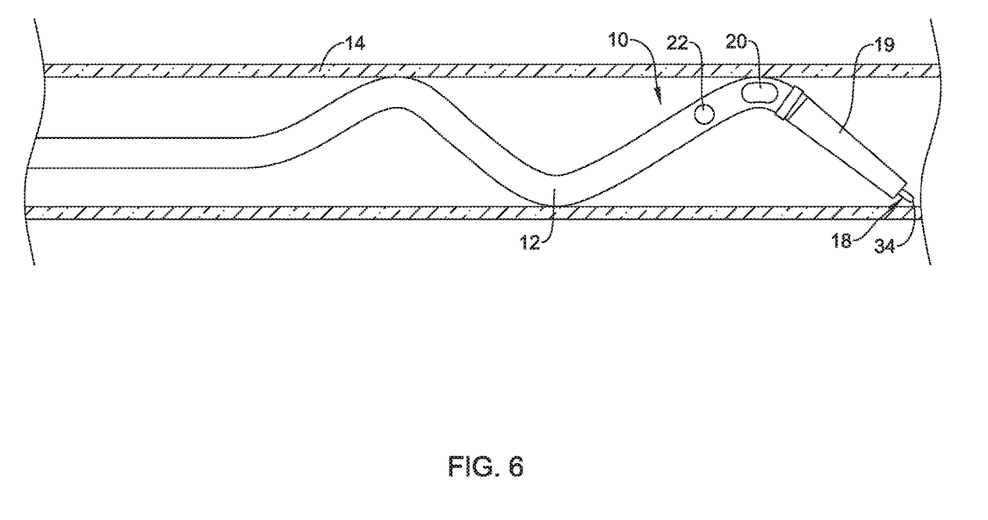

The catheter shaft 12 can be advanced over the helical distal region 34 as shown in FIGS. 5-6. Alternatively, the accessory device 18 can be advanced through the catheter shaft 12 until at least a portion of the helical distal region 34 is positioned adjacent to the distal tip region 19. Because of the flexural rigidity of the helical distal region 34 relative to that of the catheter shaft 12, disposing the helical distal region 34 of the accessory device 18 within the catheter shaft 12 may result in the catheter shaft 12 (e.g., the distal portion thereof and/or the distal tip region 19) taking a shape that resembles the shape of the helical distal region 34. For example, taking a shape that resembles the shape of the helical distal region 34 may bring the catheter shaft 12 (e.g., the distal tip region 19, the first orifice 20, the second orifice 22, or combinations thereof) to a position at or adjacent to the wall of the blood vessel 14. When arranged with the helical distal region 34 within the catheter shaft 12, the catheter shaft 12 may be translated, rotated, or combinations thereof in order to position the distal tip region 19, the first orifice 20, the second orifice 22, or combinations thereof adjacent to a target (e.g., thrombus). Likewise, the accessory device 18 may also be translated, rotated, or combinations thereof in order to position the distal tip region 19, the first orifice 20, the second orifice 22, or combinations thereof adjacent to a target (e.g., thrombus). In some instances, the first orifice 20 and the second orifice 22 of the catheter shaft 12 may be aligned along the same side of the catheter shaft 12. Thus, when used with the accessory device 18, it may be possible to use this feature of the catheter shaft 12 so that the orifices 20/22 can face the wall of the blood vessel 14 while being bent or otherwise shifted to a position adjacent to the wall of the blood vessel 14.

Figure 7:
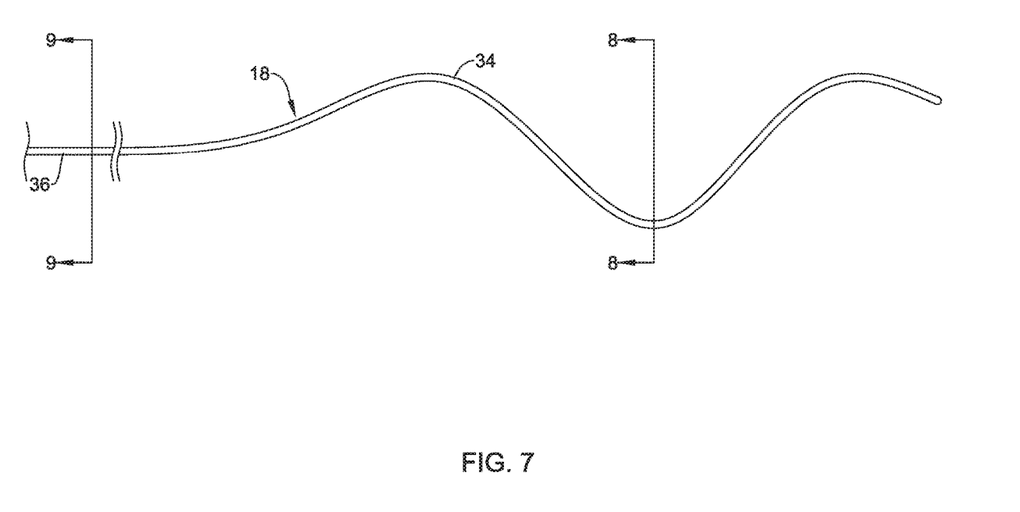
FIG. 7 is a side view of an example accessory device.

A portion of (e.g., the distal end of) the accessory device 18 is shown in FIG. 7. Here it can be seen that in addition to the helical distal region 34, the accessory device 18 may include a drive shaft or proximal end region 36. In at least some instances, the accessory device 18 is formed from a wire and the wire can be manipulated during manufacturing to form the helical distal region 34. For example, a portion of the wire can be cold-formed around a mandrel to form the helical distal region 34. Other methods are contemplated. The pitch, diameter, number of turns, and the like can vary. For example, the helical distal region 34 may have a substantially constant pitch. Alternatively, the pitch can vary along the length of the helical distal region 34. In some of these and in other instances, the helical distal region 34 can define a substantially cylindrical region having a substantially constant diameter. In other instances, the helical distal region 34 can have a different shape and/or the diameter can vary. For example, the helical distal region 34 or a portion thereof can have a conical shape. In addition, the helical distal region 34 may have one or more turns or revolutions about the longitudinal axis of the accessory device 18. For example, the helical distal region 34 may make one complete turn, two complete turns, three complete turns, four complete turns, or more about the longitudinal axis of the accessory device 18. In some of these and in other instances, the helical distal region 34 may also include a portion of an additional turn. In some instances, the helical region 34 may make less than one full revolution (e.g., one quarter turn, one half turn, three quarters of a turn, etc.).

In some instances, and as the name suggests, the helical distal region 34 may be understood as having a helical shape. Because of this, when disposed in a cylindrical body lumen, the helical shape may generally trace this inside surface of the body lumen. In other words, the majority of the helical distal region 34 may lie along and be in contact with the wall of the blood vessel 14. While the helical distal region 34 is described as having a helical shape, other variations are contemplated. For example, instead of having a substantially helical shape, the helical distal region 34 can have a series of outward and inward bends. Such a shape may zig-zag radially inward and outward so as to result in one or more distinct points of contact with the wall of the blood vessel 14. Other shapes are contemplated.

The accessory device 18 may also be formed as a guidewire and, thus, may include structural features that may be appropriate for a guidewire. For example, the proximal end region 36, the helical distal region 34, or both may take the form of or otherwise include a core wire. The diameter of the core wire may be constant. Alternatively, the core wire may include one or more tapers or tapered regions. In some instances, the tapered region(s) may extend to portions of the accessory device 18 that form the helical distal region 34. In some instances, a coil or spring tip (which may include a solder ball distal end) may be disposed over the tapered regions(s). Alternatively, a polymer tip may be disposed over the tapered region(s). These are just examples. Other structural arrangements are contemplated.

Figure 8:
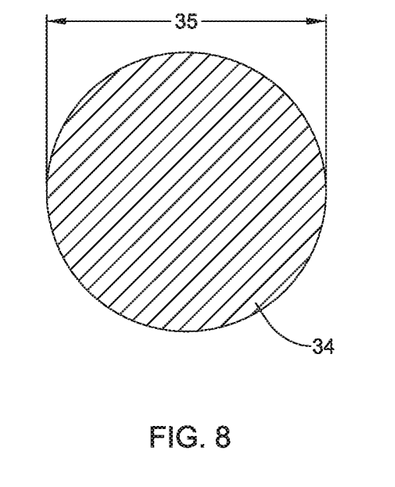
FIG. 8 is a cross-sectional view taken through 8-8 in FIG. 7.
Figure 9:
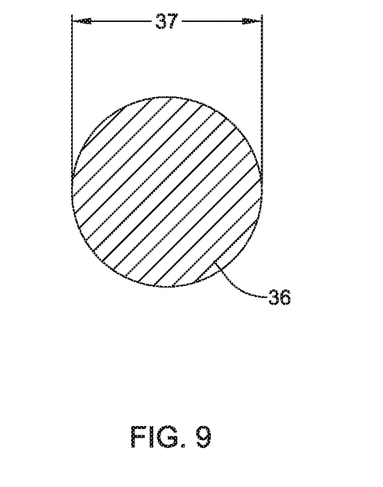
FIG. 9 is a cross-sectional view taken through 9-9 in FIG. 7.

In some instances, the helical distal region 34 may have a stiffness, outer diameter, or both that are different than those of the proximal end region 36. This may allow the helical distal region 34 to alter the shaft of the catheter shaft 12, which may be more flexible than the helical distal region 34. For example, the helical distal region 34 may have a first flexural rigidity or stiffness, the proximal end region 36 may have a second stiffness, and the first stiffness is different than the second stiffness. In at least some instances, the first stiffness is greater than the second stiffness (e.g., the helical distal region 34 is stiffer than the proximal end region 36). The helical distal region 34 may also have a flexural rigidity or stiffness that is greater than the catheter shaft 12. This may allow the catheter shaft 12 to take the shape of the helical distal region 34 when the catheter shaft 12 is positioned along the helical distal region 34. In some of these and in other instances, the helical distal region 34 may have a first outer diameter 35, such as shown in the cross-section taken along 8-8 illustrated in FIG. 8, the proximal end region 36 may have a second outer diameter 37, such as shown in the cross-section taken along 9-9 illustrated in FIG. 9, and the first outer diameter 35 is different than the second outer diameter 37. In at least some instances, the first outer diameter 35 is greater than the second outer diameter 37 (e.g., the helical distal region 34 has a larger outer diameter than the proximal end region 36). Differences in stiffness between the helical distal region 34 and the proximal end region 36 may be accomplished using laser or saw-cut slots. For example, the proximal end region 36 may include slots while the helical distal end region 34 may be free of slots. Alternatively, both the proximal end region 36 and the helical distal end region 34 may include slots with the slots in the proximal end region 36 conferring greater flexibility (e.g., via greater slot density, greater slot length, greater slot width, etc.).

It can be appreciated that as the ratio of the flexural rigidity or stiffness of the helical distal region 34 relative to the proximal end region 36 varies, the positioning of the helical distal region 34 relative to the proximal end region 36 within the blood vessel may vary, for example when encountering a bend in the blood vessel 14. For example, in instances where the ratio of the flexural rigidity or stiffness of the helical distal region 34 relative to the proximal end region 36 is increased (e.g., the stiffness of the proximal end region is reduced), when the accessory device 18 encounters a bend in the blood vessel 14, the helical distal region 34 may deflect at a greater angle than when the ratio is smaller.

Figure 10:
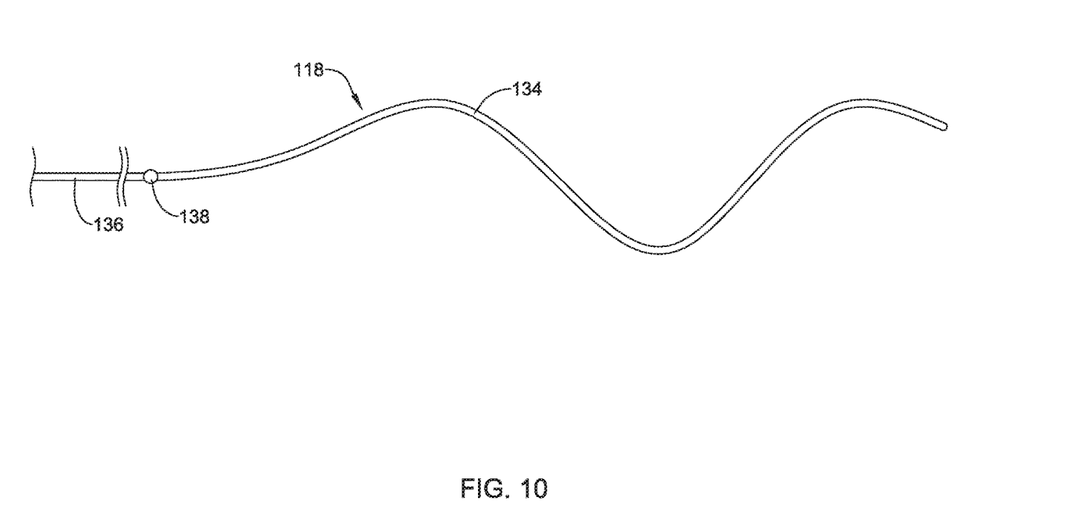
FIG. 10 is a side view of an example accessory device.

In some instances, the accessory device 18 may be formed form a single shaft. Alternatively, the accessory device 18 may be formed from one or more shafts that are joined together. For example, FIG. 10 illustrates another example accessory device 118 that may be similar in form and function to other accessory devices disclosed herein. The accessory device 118 may include a helical distal region 134 and a proximal end region 136. In this example, the helical distal region 134 is coupled to the proximal end region 136 at a joint (e.g., a point where the helical distal region 134 and the proximal end region 136, when constructed as separate structures, come together and are secured to one another) or otherwise by a joint member 138. The joint member 138 may be a bond point (e.g., a weld, adhesive bond, mechanical bond, etc.). Alternatively, the joint member 138 may take the form of a sleeve that is disposed over a portion of the proximal end region 136 and the helical distal region 134 and then joined thereto.

Figure 11:
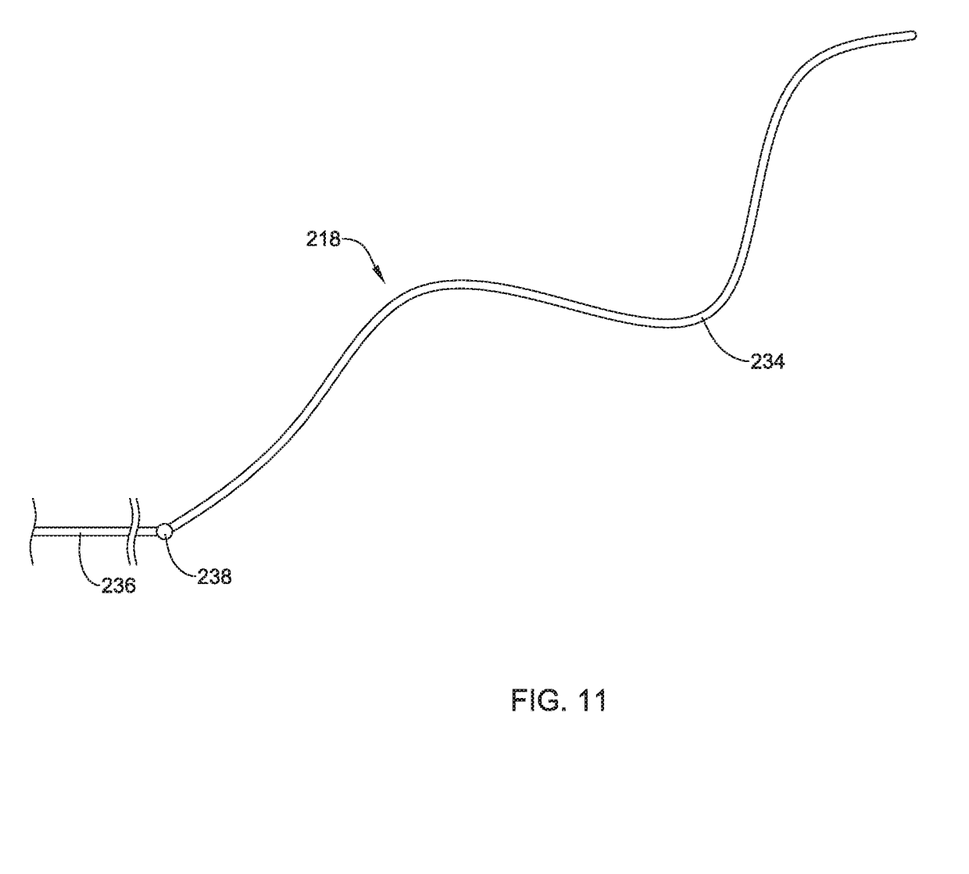
FIG. 11 is a side view of an example accessory device.

FIG. 11 illustrates another example accessory device 218 that may be similar in form and function to other accessory devices disclosed herein. The accessory device 218 may include a helical distal region 234 and a proximal end region 236. The helical distal region 234 may be coupled to the proximal end region 236 by a joint member 238. In this example, the helical distal region 234 is oriented at an angle relative to the proximal end region 236. For example, the helical distal region 34/134 of the accessory devices 18/118 disclosed herein may be understood as being generally cylindrical and being coaxial with the proximal end regions 36/136 thereof. The helical distal region 234 may be generally cylindrical, like other helical distal regions disclosed herein. However, accessory device 218 may differ from these accessory devices in that the helical distal region 234 may be oriented at a non-zero angle relative to the longitudinal axis of the proximal end region 236. Because of this, the helical distal region 234 may be considered to not be coaxial with the proximal end region 236.

The materials that can be used for the various components of the system 10 (and/or other systems disclosed herein) may include those commonly associated with medical devices. For simplicity purposes, the following discussion makes reference to the catheter shaft 12 and other components of the system 10. However, this is not intended to limit the devices and methods described herein, as the discussion may be applied to other similar devices components of systems disclosed herein.

The catheter shaft 12 and/or other components of the system 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY®

ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system 10 to achieve the same result.

In some embodiments, a degree of Magnetic Resonance Imaging (MRI) compatibility is imparted into the system 10. For example, the system 10, or portions thereof, may be made of a material that does not substantially distort the image and create substantial artifacts (e.g., gaps in the image). Certain ferromagnetic materials, for example, may not be suitable because they may create artifacts in an MRI image. The system 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

U.S. Patent Application No. 62/303,193 filed Mar. 3, 2016 is herein incorporated by reference.

U.S. Patent Application No. 62/396,803 filed Sep. 19, 2016 is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A thrombectomy catheter system, comprising:
   a catheter shaft having a proximal portion, a distal portion, and a lumen extending at least partially through the catheter shaft;
   a high pressure tube disposed within the lumen, the high pressure tube being designed for communication with a fluid source;
   a fluid jet emanator coupled to the high pressure tube, the fluid jet emanator having at least one jet orifice;
   wherein the catheter shaft includes a first orifice disposed proximally of a distal end of the catheter shaft and a second orifice disposed proximally of the first orifice; and
   an accessory device disposed within the lumen, the accessory device including a helical distal region, the helical distal region being adapted to cause the distal portion of the catheter shaft to take a shape that resembles the shape of the helical distal region when the helical distal region is disposed within the catheter shaft.

2. The thrombectomy catheter system of claim 1, wherein the accessory device comprises a guidewire having a proximal region.

3. The thrombectomy catheter system of claim 2, wherein the proximal region has a first diameter, wherein the helical distal region has a second diameter, and wherein the first diameter is different than the second diameter.

4. The thrombectomy catheter system of claim 3, wherein the second diameter is larger than the first diameter.

5. The thrombectomy catheter system of claim 2, wherein the proximal region has a first stiffness, wherein the helical distal region has a second stiffness, and wherein the first stiffness is different than the second stiffness.

6. The thrombectomy catheter system of claim 5, wherein the second stiffness is greater than the first stiffness.

7. The thrombectomy catheter system of claim 2, wherein the proximal region is attached to the helical distal region at a joint.

8. The thrombectomy catheter system of claim 2, wherein the proximal region has a longitudinal axis and wherein the helical distal region extends from the proximal region at a non-zero angle relative to the longitudinal axis.

9. A thrombectomy catheter system, comprising:
   a catheter shaft having a proximal portion, a distal portion, and a lumen extending at least partially through the catheter shaft;
   wherein the catheter shaft includes an inflow orifice disposed proximally of a distal end of the catheter shaft and an outflow orifice disposed proximally of the inflow orifice; and
   a guidewire disposed within the lumen, the guidewire including a proximal region and a helical distal region, the helical distal region being adapted to cause the distal portion of the catheter shaft to take a shape that resembles the shape of the helical distal region when the helical distal region is disposed within the catheter shaft.

10. The thrombectomy catheter system of claim 9, wherein the proximal region has a first diameter, wherein the helical distal region has a second diameter, and wherein the first diameter is different than the second diameter.

11. The thrombectomy catheter system of claim 10, wherein the second diameter is larger than the first diameter.

12. The thrombectomy catheter system of claim 9, wherein the proximal region has a first stiffness, wherein the helical distal region has a second stiffness, and wherein the first stiffness is different than the second stiffness.

13. The thrombectomy catheter system of claim 12, wherein the second stiffness is greater than the first stiffness.

14. The thrombectomy catheter system of claim 9, wherein the proximal region is attached to the helical distal region at a joint.

15. The thrombectomy catheter system of claim 9, wherein the proximal region has a longitudinal axis and wherein the helical distal region extends from the proximal region at a non-zero angle relative to the longitudinal axis.

16. A method for orienting a catheter, the method comprising:
   disposing a thrombectomy catheter within a body lumen, the thrombectomy catheter comprising:
      a catheter shaft having a proximal portion, a distal portion, and a lumen extending at least partially through the catheter shaft, a high pressure tube disposed within the lumen, the high pressure tube being designed for communication with a fluid source, a fluid jet emanator coupled to the high pressure tube, the fluid jet emanator having at least one jet orifice, and wherein the catheter shaft includes a first orifice disposed proximally of a distal end of the catheter shaft and a second orifice disposed proximally of the first orifice;

wherein disposing a thrombectomy catheter within a body lumen includes disposing the distal portion at a first position relative to a wall of the body lumen;

disposing an accessory device within the lumen, the accessory device including a proximal region and a helical distal region, the helical distal region being adapted to cause the distal portion of the catheter shaft to take a shape that resembles the shape of the helical distal region when the helical distal region is disposed within the catheter shaft;

wherein disposing an accessory device within the lumen includes arranging the helical distal region so that at least a portion of the helical distal region is disposed adjacent to the wall of the body lumen;

wherein disposing an accessory device within the lumen includes shifting the catheter shaft to a second position that is closer to the wall of the body lumen than the first position.

17. The method of claim 16, wherein shifting the catheter shaft to a second position includes moving the first orifice to a position adjacent to the wall of the body lumen.

18. The method of claim 16, wherein shifting the catheter shaft to a second position includes moving the helical distal region of the accessory device into the catheter shaft, thereby arranging at least a portion of the catheter shaft into a helical configuration.

19. The method of claim 16, wherein the proximal region of the accessory device has a first diameter, wherein the helical distal region has a second diameter, and wherein the second diameter is greater than the first diameter.

20. The method of claim 16, wherein the proximal region of the accessory device has a first stiffness, wherein the helical distal region has a second stiffness, and wherein the second stiffness is greater than the first stiffness.

* * * * *